United States Patent [19]

Kolassa et al.

[11] Patent Number: 5,201,935
[45] Date of Patent: Apr. 13, 1993

[54] CYCLOHEXENONE DERIVATIVES

[75] Inventors: Dieter Kolassa, Ludwigshafen; Juergen Kasi, Boehl-Iggelheim; Thomas Kuekenhoehner, Frankenthal; Norbert Meyer, Ladenburg; Karl-Otto Westphalen, Speyer; Bruno Wuerzer, Otterstadt, all of Fed. Rep. of Germany

[73] Assignee: BASF Aktiengesellschaft, Ludwigshafen, Fed. Rep. of Germany

[21] Appl. No.: 934,304

[22] Filed: Aug. 26, 1992

Related U.S. Application Data

[60] Continuation of Ser. No. 619,997, Nov. 30, 1990, abandoned, which is a division of Ser. No. 572,357, Sep. 19, 1989, Pat. No. 5,034,047.

[30] Foreign Application Priority Data

Sep. 30, 1988 [DE] Fed. Rep. of Germany ....... 3833264

[51] Int. Cl.$^5$ ..................... A01N 43/80; C07D 413/04
[52] U.S. Cl. .................................... 504/271; 546/275; 546/280; 548/243
[58] Field of Search .............................. 71/88; 548/243

[56] References Cited

U.S. PATENT DOCUMENTS

| | | |
|---|---|---|
| 4,623,381 | 11/1986 | Jahn et al. ............................... 71/94 |
| 4,624,696 | 11/1986 | Keil et al. ............................. 546/275 |
| 4,704,157 | 11/1987 | Conway et al. ......................... 71/90 |
| 4,761,172 | 8/1988 | Jahn et al. ............................. 71/88 |
| 4,761,486 | 8/1988 | Zeeh et al. ............................. 549/9 |
| 4,983,210 | 1/1991 | Rheinheimer et al. ............. 546/275 |
| 5,034,047 | 7/1991 | Kolassa et al. ..................... 546/275 |

FOREIGN PATENT DOCUMENTS 0162224  11/1985  European Pat. Off. .

OTHER PUBLICATIONS

Hamaguchi, et al., "Chemical Abstracts", vol. 110, 1989, Col. 110:231623m.

*Primary Examiner*—C. Warren Ivy
*Assistant Examiner*—James H. Turnipseed
*Attorney, Agent, or Firm*—Keil & Weinkauf

[57] ABSTRACT

Cyclohexenone derivatives of the general formula I

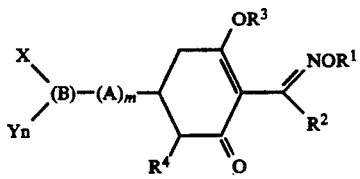

where the substituents have the following meanings:
$R^1$ substituted or unsubstituted $C_1$–$C_6$-alkyl, $C_3$–$C_6$-alkenyl or $C_3$–$C_6$-alkynyl, phenyl, benzyl or thenyl;
$R^2$ substituted or unsubstituted $C_1$–$C_6$-alkyl, $C_3$–$C_6$-alkenyl, $C_3$–$C_6$-alkynyl or phenyl;
$R^3$ hydrogen, $C_1$–$C_6$-alkyl, $C_1$–$C_{10}$-alkylcarbonyl, $C_1$–$C_6$-alkylsulfonyl, $C_1$–$C_4$-trialkylsilyl, $C_1$–$C_4$-dialkylphosphonyl, $C_1$–$C_4$-dialkylthiophosphonyl, $C_3$–$C_6$-alkenyl, $C_3$–$C_6$-alkenylcarbonyl, $C_3$–$C_6$-alkynyl or
substituted or unsubstituted benzoyl- or phenylsulfonyl;
$R^4$ hydrogen, cyano, halogen, $C_1$–$C_6$-alkyl or $C_1$–$C_6$-alkoxycarbonyl;
A a substituted or unsubstituted $C_1$–$C_4$-alkylene chain in which a methylene group may be replaced by an oxygen or sulfur atom;
m 0 or 1;
B a 5-membered mono- or diunsaturated heterocycle containing up to 2 nitrogen atoms and/or up to one oxygen or sulfur atom;
substituted or unsubstituted $C_1$–$C_6$-alkyl, $C_2$–$C_6$-alkenyl or $C_2$–$C_6$-alkynyl;
$C_1$–$C_4$-alkoxy, $C_1$–$C_4$-alkylthio, $C_3$–$C_6$-alkenyloxy or $C_3$–$C_6$-alkynyloxy;
n 1, 2 or 3;
Y not denoting hydrogen when m is 0, B is isoxazol-5-yl and X is 3-($C_3$–$C_6$-cycloalkyl), and environmentally acceptable salts thereof, processes for their manufacture, and their use as herbicidal agents.

4 Claims, No Drawings

CYCLOHEXENONE DERIVATIVES

This application is a continuation of application Ser. No. 07/619,997, filed on Nov. 30, 1990, now abandoned, which is a division of Ser. No. 07/572,357, filed Sep. 19, 1989 now U.S. pat. No. 5,034,047.

The present invention relates to novel cyclohexenone derivatives of the general formula I

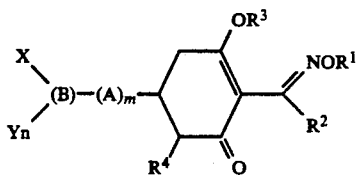

where is $C_1-C_6$-alkyl, $C_3-C_6$- alkenyl or $C_3-C_6$-alkynyl and these groups may carry from one to three of the following radicals: halogen, $C_1-C_4$-alkoxy, $C_1-C_4$-alkylthio and/or phenyl, and the phenyl group in turn may be monosubstituted to trisubstituted by halogen, $C_1-C_4$-alkyl, $C_1-C_4$-alkoxy, $C_1-C_4$-alkylthio, $C_1-C_4$-haloalkyl and/or cyano; phenyl, benzyl or thenyl, where the aromatic nuclei may carry from one to three of the following radicals halogen, $C_1-C_4$-alkyl, $C_1-C_4$-alkoxy, $C_1-C_4$-alkylthio, $C_1-C_4$-haloalkyl, nitro and/or cyano;

$R^2$ is $C_1-C_6$-alkyl, $C_3-C_6$-alkenyl, $C_3-C_6$-alkynyl or phenyl, and these groups may carry from one to three of the following radicals halogen, $C_1-C_4$-alkoxy, $C_1-C_4$-alkylthio and/or cyano;

$R^3$ is hydrogen, $C_1-C_6$-alkyl, $C_1-C_{10}$-alkylcarbonyl, $C_1-C_6$-alkylsulfonyl, $C_1-C_4$-trialkylsilyl, $C_1-C_4$-dialkylphosphonyl, $C_1-C_4$-dialkylthiophosphonyl, $C_3-C_6$-alkenyl, $C_3-C_6$-alkenylcarbonyl or $C_3-C_6$-alkynyl or a benzoyl or phenylsulfonyl group which may be monosubstituted to trisubstituted by halogen, nitro, cyano, $C_1-C_4$-alkyl, $C_1-C_4$-haloalkyl, $C_1-C_4$-alkoxy and/or $C_1-C_4$-alkylthio;

$R^4$ is hydrogen, cyano, halogen, $C_1-C_6$-alkyl or $C_1-C_6$-alkoxycarbonyl;

A is a $C_1-C_4$-alkylene chain in which a methylene group may be replaced by an oxygen or sulfur atom and which may carry one or two of the following substituents: $C_1-C_4$-alkyl, $C_1-C_4$-alkoxy, $C_1-C_4$-alkylthio and/or halogen;

m is 0 or 1,

B is a 5-membered monounsaturated or diunsaturated heterocyclic radical having not more than 2 nitrogen atoms and/or not more than one oxygen or sulfur atom, X is a 3-membered to 7-membered cycloalkyl radical or a 5-membered to 7-membered cycloalkenyl radical, and a methylene group in these ring systems may be replaced by an oxygen or sulfur atom; a phenyl ring or a 5-membered or 6-membered heteroaromatic radical, where these rings may carry from one to three of the following groups: $C_1-C_4$-alkyl, $C_1-C_4$-alkoxy, $C_1-C_4$-alkylthio, $C_1-C_4$-haloalkyl, halogen, cyano and/or nitro or, if B is isoxazolinyl and m is zero, also hydrogen;

Y is hydrogen, halogen, cyano or nitro;

$C_1-C_6$-alkyl, $C_2-C_6$-alkenyl or $C_2-C_6$-alkynyl, and these groups may carry from one to three of the following radicals: phenyl, halogen, $C_1-C_4$-alkoxy and/or $C_1-C_4$-alkylthio, $C_1-C_4$-alkoxy, $C_1-C_4$-alkylthio, $C_3-C_6$-alkenyloxy or $C_3-C_6$-alkynyloxy;

n is 1, 2 or 3 and Y is not hydrogen if m is 0, B is isoxazol-5-yl and

X is 3-($C_3-C_6$-cycloalkyl), and their environmentally compatible salts

The present invention furthermore relates to the preparation of the compounds I, their use as herbicides and mixtures for controlling undesirable plant growth which contain the compounds of the formula I.

The compounds of the formula I may occur in a plurality of tautomeric forms, all of which are embraced by the claim and, where $R^3$ is H, may be represented as follows:

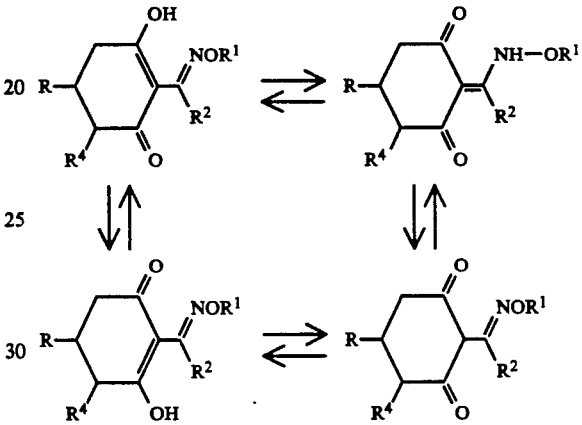

In this scheme, as in all the equations below, the radical

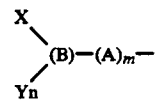

is denoted by R for greater clarity

The herbicidal action of 3-hydroxy-2-cyclohexen-1-one oxime ether derivatives which carry a 5-membered heterocyclic radical in the 5-position is disclosed in EP-A 125 094, EP-A 162 224 and EP-A 238 021.

It is an object of the present invention to provide compounds which can be used at lower application rates, are better tolerated by crop plants (greater selectivity) and have a good action against weeds.

We have found that this object is achieved by the cyclohexenones I defined at the outset.

These novel cyclohexenone derivatives have a good herbicidal action preferably against species from the family of the grasses (Gramineae) They are tolerated and therefore have selective action in broad-leaved crops and in monocotyledons which do not belong to the Gramineae. They furthermore include compounds which also have a selective action in graminaceous crops such as wheat, barley and rice and at the same time control undesirable grasses. The novel cyclohexenone derivatives of formula I also have a growth-regulating action against species from the family of the grasses.

The compounds I are prepared in four reaction steps according to the following scheme:

The compounds I are prepared in four reaction steps according to the following scheme:

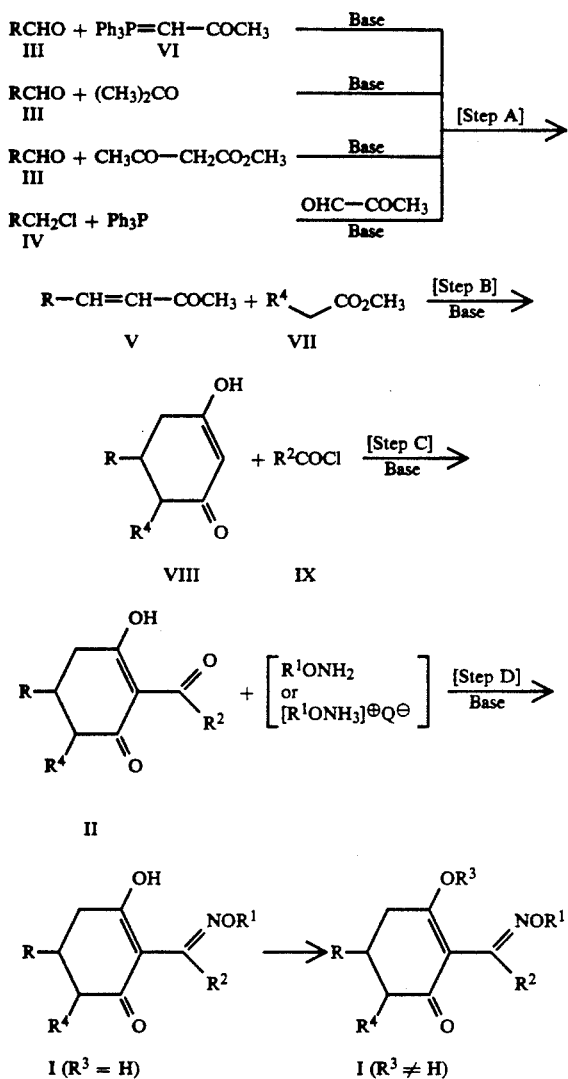

The required intermediates are obtainable by many methods which have been described in a large number of patent publications, for example EP-A 125 094, EP-A 150 433 or EP-A 238 021.

A) Step A comprises the preparation of the vinyl ketones of formula V.

Alternatively, for example, the following processes are possible:

An aldehyde of the formula III is reacted with acetone in the presence of a base or with a Wittig reagent of the formula VI or with ethyl acetoacetate in the presence of a base to give the vinyl ketone of the formula V.

Halomethyl compounds of the formula IV may also be used, these compounds first being converted into the phosphonium salts and then being reacted with methylglyoxal to give the desired vinyl ketones of the formula V.

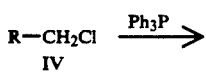
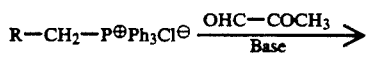
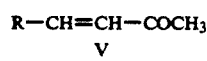

B) Step B relates to the synthesis of the 3-hydroxy-2-cyclohexen-1-ones of the formula VIII. For this purpose, the vinyl ketones of the formula V are reacted with, for example, an ester derivative of the formula VII in the presence of a base, the desired compounds of the formula VIII being formed.

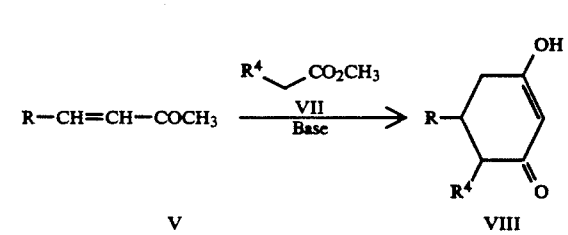

C) Step C gives the 2-acyl-3-hydroxy-2-cyclohexen-1-ones of the formula II. For this purpose, the derivatives of the formula VIII are reacted with an acyl chloride of the formula IX in the presence of a base to give O-acylated derivatives of the formula X, which are then subjected to a rearrangement reaction in the presence of a Lewis acid or of a base, such as imidazole, pyridine or 4-N,N-dimethylaminopyridine, to give the C-acylated compound of the formula II.

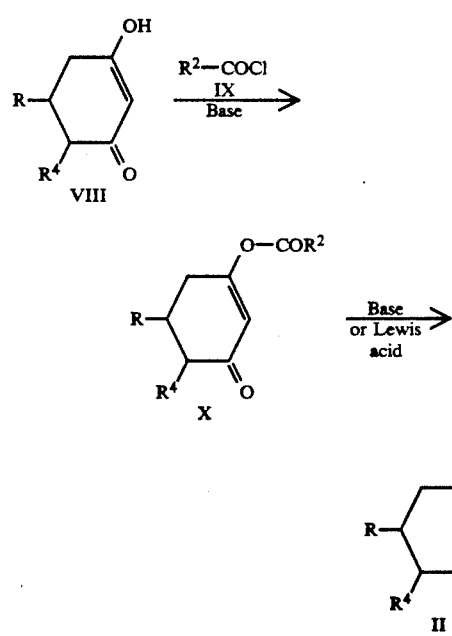

D) Step D relates to the preparation of the compounds of the formula I, which are obtained from the 2-acyl-3-hydroxy-2-cyclohexen-1-ones II by reaction with an alkoxyammonium salt of the formula $R^1ONH_2 \cdot HQ$, where Q is a suitable leaving group, such as chloride. Alternatively, it is also possible to use the free alkoxyamine $R^1ONH_2$.

Compounds which contain a substituent $R^3$ which is not hydrogen are obtainable from compounds of the formula I where $R^3$ is H in a conventional manner as described below.

In the case of the ethers, esters and sulfones, the compounds of the formula I where $R^3$ is H are reacted with a corresponding alkylating, acylating or sulfonating agent.

Other suitable starting materials for this purpose are the alkali metal salts of the compounds of the formula I, which are obtained by reaction with an alkali metal hydroxide, an alkali metal alcoholate or an alkali metal hydride.

If, in formula I, $R^3$ is another inorganic or organic cation, these compounds are obtainable from the alkali metal salts using transition metal salts or organic bases. Examples of these are manganese chloride, copper chloride, zinc chloride and iron chloride and the corresponding sulfates, as well as magnesium methylate, magnesium ethylate, calcium methylate and calcium ethylate.

The majority of the heterocyclic aldehydes III and chloromethyl compounds IV required as starting materials are novel but can be prepared by conventional processes.

The isoxazoles are prepared, for example, under the conditions described in DE-A 2 754 832. They are obtainable from aldoximes by 1,3-dipolar cycloaddition with propargyl alcohols or propargyl halides. The 5-hydroxymethyl-substituted isoxazoles can be converted into the 5-formyl derivative by conventional oxidation processes. The regioisomers which are bonded in the 3- or 4-position can be prepared, inter alia, according to Baraldi et al., J. Het. Chem 19 (1982), 557 and Bertini et al., J. Chem Soc. Perkin Trans I 1976, 570.

Syntheses of 1,3-oxazoles are described in The Chemistry of Penicillins.

1,3-Thiazoles which are bonded in the 4- or 5-position are obtainable, for example, by processes described by A. Beukö et al., Liebigs Ann. Chem. 717 (1968), 148–153.

Syntheses of 1,2,4-oxadiazoles are described in, for example, Chem. Ber. 17 (1889), 1685 and Tetrahedron Lett. (1961), 587–589.

With regard to the use of the compounds I in accordance with regulations, the radicals below are preferred substituents.

Alkyl groups R are methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, ethyl and propyl being preferred.

Alkenyl groups in this position are 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 2-ethyl-2-butenyl, 1-ethyl-3-butenyl, 2-ethyl-3-butenyl, 1,2-trimethyl-2-propenyl, 1-ethyl-1-methyl-2-propenyl and 1-ethyl-2-methyl-2-propenyl, in particular 2-propenyl and 2-butenyl.

Preferred alkynyl radicals R are 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, in particular 2-propynyl and 2-butynyl.

These alkyl, alkenyl and alkynyl groups may be substituted by from one to three of the following groups: halogen atoms, such as bromine and iodine, preferably however from one to three fluorine and/or chlorine atoms, (E)-3-chloroprop-2-enyl being particularly preferred; alkoxy, such as methoxy, ethoxy, propoxy, 1-methylethoxy, butoxy, 1-methylpropoxy, 2-methylpropoxy and 1,1-dimethylethoxy, in particular one or two methoxy or ethoxy groups;

Alkylthio, such as methylthio, ethylthio, propylthio, 1-methylethylthio, butylthio, 1-methylpropylthio, 2-methylpropylthio and 1,1-dimethylethylthio, one or two ethylthio groups being preferred, and/or a phenyl ring which, in addition to the abovementioned halogen atoms, alkyl groups, alkoxy groups and alkylthio groups, may also carry cyano and haloalkyl, such as fluoromethyl, difluoromethyl, trifluoromethyl, chloromethyl, dichloromethyl, richloromethyl, difluorochloromethyl, 1-fluoroethyl, 2-fluoroethyl, 1,1-difluoroethyl, 1,1,2-trifluoroethyl, 1,2,2-trifluoroethyl and 2,2,2-trifluoroethyl; in particular, the phenyl ring is unsubstituted or substituted in the 4-position by fluorine, chlorine, methyl, trifluoromethyl, or 1,1-dimethylethyl and/or in the 2-position by chlorine or methoxy.

$R^1$ may furthermore be phenyl, thenyl or benzyl, and the aromatic nuclei may also be substituted by nitro, cyano and/or alkyl groups, such as methyl, ethyl, propyl, 1-methylethyl, butyl, 1-methylpropyl, 2-methylpropyl and 1,1-dimethylethyl, in addition to the abovementioned halogen atoms, alkoxy groups, alkylthio groups and haloalkyl groups. The 5-chlorothenyl radical is particularly preferred.

The alkyl, alkenyl and alkynyl groups $R^2$ and the phenyl radical $R^2$ and its substituents have the same general and particular meanings as $R^1$.

Suitable radicals $R^3$ in addition to the abovementioned alkyl, alkenyl and alkynyl groups are radicals of saturated and unsaturated carboxylic acids, such as acetyl, propionyl, butyryl and pivaloyl, in particular acetyl and butyryl; and alkylsulfonyl, alkylsilyl, alkylphosphonyl or alkylthiophosphonyl groups, the alkyl radicals preferably being methyl; ethyl, 1-methylethyl and 1,1-dimethylethyl, and benzoyl- and phenylsulfonyl. The last-mentioned aromatic radicals may be monosubstituted to trisubstituted. The possible substituents correspond to the substituents stated under $R^1$.

Suitable radicals $R^4$ in addition to hydrogen and cyano are the halogen atoms and alkyl groups already mentioned for R and alkoxycarbonyl groups, such as methoxycarbonyl, ethoxycarbonyl, propoxycarbonyl, 1-methylethoxycarbonyl, butoxycarbonyl, 1-methylpropylcarbonyl, 2-methylpropylcarbonyl and 1,1-dimethylethoxycarbonyl, but in particular methoxycarbonyl and ethoxycarbonyl.

Preferred radicals $R^4$ are hydrogen, cyano and methoxycarbonyl.

A is an alkylene, alkyleneoxyalkylene or alkylenethioalkylene chain having up to four members. Examples of these are methylene, ethylene, propylene, butylene, methyleneoxymethylene, methyleneoxyethylene, methylenethiomethylene, methylenethioethylene, propyleneoxy, propylenethio, ethyleneoxy, ethylenethio, methyleneoxy, methylenethio, oxy and thio bridges.

The compounds of the formula I preferably contain no bridge A or a 1-membered or 2-membered bridge A.

The 5-membered heterocyclic radicals B are rings such as dihydrofuranyl, dihydrothienyl, pyrrolinyl, pyrazolinyl, imidazolinyl, isoxazolinyl, oxazolinyl, isothiazolinyl, thiazolinyl, furanyl, thienyl, pyrrolyl, pyrazolyl, isoxazolyl, oxazolyl, isothiazolyl, thiazolyl, oxadiazolyl and thiadiazolyl.

Particularly preferred compounds of the formula I are those in which a 4,5-dihydroisoxazolyl ring is bonded at its 4- or 5-position by one of the abovementioned bridges to the cyclohexenone system, and those in which one of the listed heteroaromatic rings is bonded directly to the cyclohexenone ring.

Suitable groups X are the following: cycloalkyl, such as cyclopropyl, cyclobutyl, cyclopentyl, cyclohexyl and cycloheptyl, preferably cyclopropyl and cyclohexyl; cycloalkenyl, for example cyclopentenyl, cyclohexenyl and cycloheptenyl, preferably cyclopentenyl and cyclohexenyl; heterocyclic aliphatic radicals, for example epoxyethyl, oxetanyl, tetrahydrofuranyl, tetrahydropyranyl, thietanyl, tetrahydrothienyl and tetrahydrothiopyranyl, preferably 3-tetrahydropylanyl, tetrahydrothiopyranyl and 1,3-dioxan-2-yl; heterocyclic alkenyl rings, including the dihydrofuranyl, dihydrothienyl, dihydropyranyl and dihydrothiopyranyl radical, but in particular the dihydropyranyl and the dihydrothiopyranyl radical; heteroaromatic groups, for example pyrrolyl, pyrazolyl, imidazolyl, triazolyl, pyridyl, pyrimidyl, pyrazinyl, pyridazinyl, quinolyl or isoquinolyl, furanyl, thienyl, isoxazolyl, oxazolyl, oxathiazolyl, isothiazolyl and thiazolyl, preferably 2-pyridyl and 2-furyl, and hydrogen, if B is isoxazolinyl.

Heteroaromatic rings may carry up to three substituents. In addition to cyano and nitro groups, the abovementioned halogen atoms, alkyl groups, haloalkyl groups, alkoxy groups and alkylthio groups are suitable for this purpose.

Yn are from one to three identical or different radicals from amongst the abovementioned alkyl, alkenyl or alkynyl groups, as well as hydrogen, halogen, cyano and nitro. In particular, alkenyl may also be vinyl or alkynyl here, especially ethynyl.

These compounds do not include those in which Y is hydrogen when B is isoxazol-5-yl, m is 0 and X is 3-($C_3$–$C_6$-cycloalkyl).

In detail, the invention embraces preferably the following structures:

a) Pyrroles of the formula

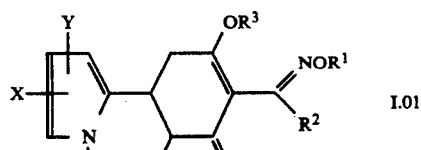

I.01

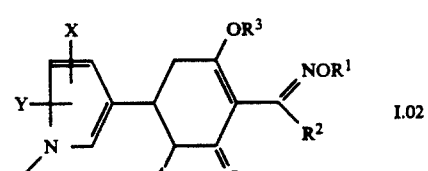

I.02 b) Furans and thiophenes of the formula

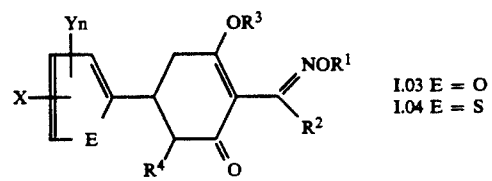

I.03 E = O
I.04 E = S

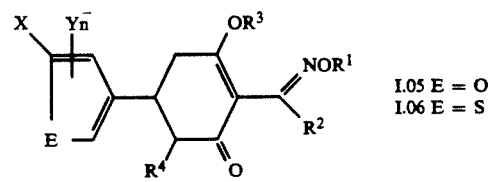

I.05 E = O
I.06 E = S c) Pyrazoles of the formula

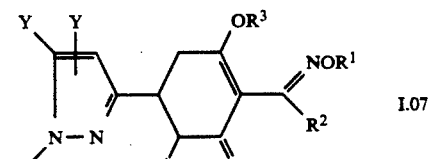

I.07

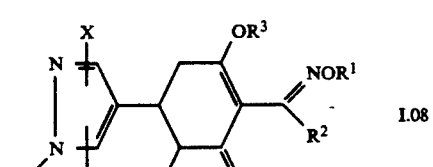

I.08

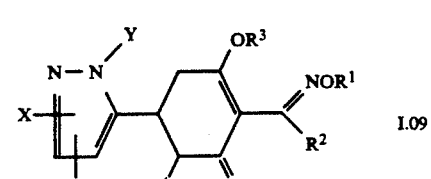

I.09 d) Isoxazoles and isothiazoles of the formula

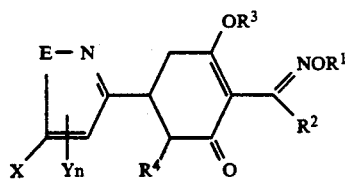 I.10 E = O
I.11 E = S

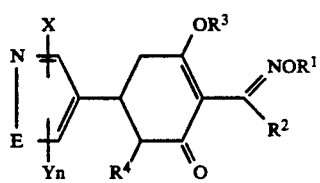 I.12 E = O
I.13 E = S

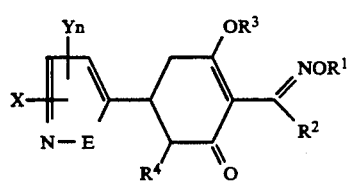 I.14 E = O
I.15 E = S e) Oxazoles and thiazoles of the formula

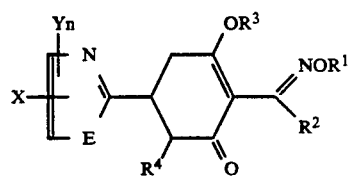 I.16 E = O
I.17 E = S

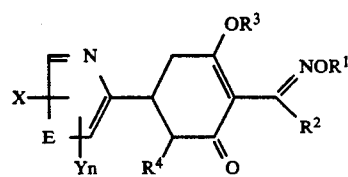 I.18 E = O
I.19 E = S

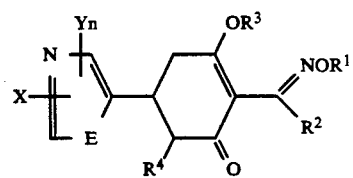 I.20 E = O
I.21 E = S f) 1,2,3-Oxadiazoles and 1,2,3-thiadiazoles of the formula

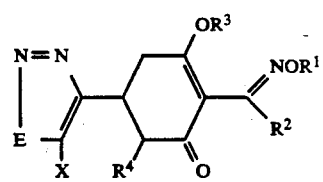 I.22 E = O
I.23 E = S

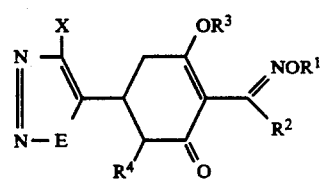 I.24 E = O
I.25 E = S g) 1,2,4-Oxadiazoles and 1,2,4-thiadiazoles of the formula

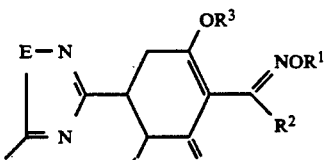 I.26 E = O
I.27 E = S

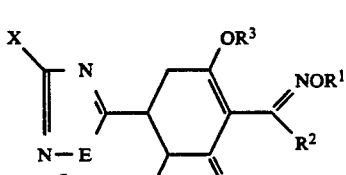 I.28 E = O
I.29 E = S h) 1,3,4-Oxadiazoles and 1,3,4-thiadiazoles of the formula

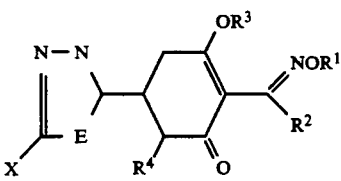 I.30 E = O
I.31 E = S i) 4,5-Dihydroisoxazolines of the formula

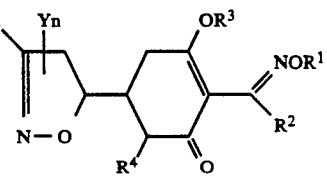 I.32

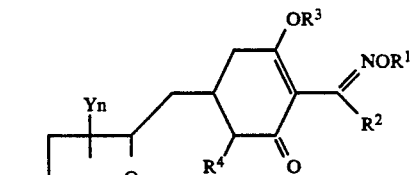 I.33

The cyclohexenone derivatives I, and herbicidal agents containing them, may be applied instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives such as methanol, ethanol, propanol, butanol, cyclohexanol, cyclohexanone, chlorobenzene, isophorone, etc., and strongly polar solvents such a N,N-dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, alkali metal and alkaline earth metal salts of dibutylnaphthalenesulfonic acid, lauryl ether sulfate, fatty alcohol sulfates, and salts of sulfated hexadecanols, heptadecanols, and octadecanols, salts of fatty alcohol glycol ethers, condensation products of sulfonated napthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapoulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90%, by weight of active ingredient.

The agents may be applied pre- or postemergence. If certain crop plants tolerate the active ingredients less well, application techniques may be used in which the herbicidal agents are sprayed from suitable equipment in such a manner that the leaves of sensitive crop plants are if possible no touched, and the agents reach the soil or the unwanted plants growing beneath the crop plants (post-directed, lay-by treatment).

The application rates depend on the objective to be achieved, the time of the year, the plants to be combated and their growth stage, and are from 0.01 to 3.0, preferably 0.05 to 1.0, kg of active ingredient per hectare.

In view of the spectrum of weeds that can be combated, the tolerance by crop plants and the desired influence on plant growth, and in view of the number of application methods possible, the compounds according to the invention may be used in a further large number of crops for removing unwanted plants. The following crops are given by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabic (Coffea canephora, Coffea liberica) | coffee plants |
| Cucumis melo | melons |
| Cynodon dactylon | Bermudagrass |
| Cucumis sativus | cucumbers |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium bitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (S. vulgare) | sorghum |

-continued

| Botanical name | Common name |
| --- | --- |
| Sorghum dochna | sorgo |
| Spinacia oleracea | spinach |
| Theobrama cacao | cacao plants |
| Trifolium pratense | red clover |
| Triticum aestivum | wheat |
| Triticum durum | durum wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the cyclohexenone derivatives of the formula I may be mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, quinolinecarboxylic acids, cyclohexenones, aryloxy- or heteroaryloxy-phenoxypropionic acids and salts, esters and amides thereof, etc.

It may also be useful to apply the cyclohexenone compounds of the formula I, either along or in combination with other herbicides, in admixture with other crop protection agents, e.g., agents for combating mixed with solutions of mineral salts used to remedy nutritional or trace element deficiencies. Non-phytotoxic oils and oil concentrates may also be added.

In the synthesis methods below, the individual steps of the synthesis are described with reference to some specific examples.

1. Preparation of the Heterocyclic Chloromethyl Compounds a) 5-Chloromethyl-3-pyrid-2-ylisoxazole 774 g of a 14% strength sodium hypochlorite solution were added to a mixture of 122 g of 2-pyridylaldoxime, 1.5 l of water, 500 ml of dichloromethane, 15 g of sodium dihydrogen phosphate dihydrate, 18 g of sodium hydrogen phosphate dihyd-rate and 150 g of propargyl chloride at 20°-25° C. Stirring was carried out for 10 hours at 25° C., the phases were separated and the aqueous phase was extracted with twice 150 ml of dichloromethane. The combined organic phases were dried over sodium sulfate and evaporated down 170 g of a brown solid were obtained The product was reacted without further purification.

b) 5-Chloromethyl-3-cyclopentyl-1,2,4-oxadiazole 100 g of hydroxylamine hydrochloride were dissolved in 360 ml of water, and 122 g of sodium bicarbonate were added a little at a time at 25° C. Thereafter, 138 g of cyclopentanecarbonitrile, dissolved in 400 ml of ethanol, were added dropwise. The reaction mixture was refluxed for 10 hours at 80° C., cooled and then evaporated down. The residue was taken up in a 1:1 mixture of ethyl acetate and water and stirred The organic phase was separated off, the aqueous phase was extracted twice with ethyl acetate and the combined organic phases were dried and evaporated down. 166 g of a white solid were obtained. This solid was added a little at a time to a mixture of 99 4 g of chloroacetyl chloride, 600 ml of toluene and 0.5 g of p-toluenesulfonic acid, which mixture had been brought to the reflux temperature for a short time. After the end of the addition, the mixture was refluxed again and the water of reaction was removed. After water no longer separated off, 250 ml of water were added. The mixture was neutralized with 10% strength sodium hydroxide solution, after which the organic phase was separated off, the aqueous phase was extracted three times with toluene and the combined organic phases were dried and evaporated down The dark brown liquid obtained was subjected to fractional distillation.

Yield: 100 g of a colorless liquid Bp. 85°-87° C./0.1 mbar.

c) 3-Tert-butyl-5-hydroxy-methyl-5-methylisoxazoline 1596 g (3.0 moles) of a 14% strength sodium hypochlorite solution were added to a mixture of 303.0 g (3.0 moles) of pivalinaldoxime, 216.0 g (3.0 moles) of 2-methylallyl alcohol, 500 ml of dichloromethane, 800 ml of water, 80.1 g (0.45 mole) of a 15 mol % disodium hydrogen phosphate solution and 23 4 g (0.15 mole) of a 5 mol % sodium dihydrogen phosphate solution at 20°-25° C. and the mixture was stirred overnight at this temperature. The organic phase was separated off and the aqueous phase was extracted twice with dichloromethane. The combined organic phases were dried over sodium sulfate and evaporated down The resulting colorless liquid was subjected to fractional distillation under reduced pressure. Yield: 401 g of a colorless oil which crystallizes on standing.

Bp. 80°-84° C./0.01 mbar.

d) 3-Tert-butyl-5-formyl-5-methylisoxazoline

A solution of 117.0 g (1.5 moles) of dimethylsulfoxide in 300 ml of dichloromethane was added dropwise to a solution of 83.8 g (0.66 mole) of oxalyl chloride in 750 ml of dichloromethane at −60° C. The reaction mixture was stirred for 15 minutes at this temperature, after which 102.6 g (0.6 mole) of 3-tert-butyl-5-hydroxymethyl-5-methylisoxazoline were added and stirring was continued for a further 15 minutes. After the dropwise addition of 303.6 g (3.0 moles) of triethylamine, the mixture was stirred for a further 10 minutes and was heated to 25° C. and 1.8 l of water were added. After 10 minutes, the organic phase was seperated off, the aqueous phase was extracted with twice 600 ml of dichloromethane and the combined organic phases were washed with three times 450 ml of a 1N hydrochloric acid and once with 450 ml of a saturated sodium carbonate solution, dried and evaporated down. 100 g of a yellow liquid were obtained, this liquid being subjected to fractional distillation under 0.2 mbar.

Yield: 77.4 g of a colorless liquid. Bp. 58°-62° C./0.4–0.2 mbar.

2. Preparation of the Vinyl Ketones V a) 4-[3-Pyrid-2-ylisoxazol-5-yl]-3-buten-2-one 100 g of 5-chloromethyl-3-pyrid-2-ylisoxazole and 175 g of triphenylphosphane were dissolved in 300 ml of chloroform and the solution was refluxed for 2 days. After the reaction mixture had been cooled and evaporated down, the residue was stirred with tert-butyl methyl ether and the brown solid was separated off and dried. 210 g of phosphonium salt were obtained, to which 113 g of a 40% strength methylglyoxal solution in water, 250 ml of water and 250 ml of dichloromethane were added. 46 g of sodium bicarbonate were added a little at a time at 25° C., after which the mixture was stirred for 1 hour, the organic phase was separated off and the aqueous phase was extracted twice with dichloromethane. The combined organic phases were evaporated down and the residue was stirred with tert-butyl methyl ether to give 100 g of a pale brown solid, which was reacted without further purification.

b)
4-[3-Tetrahydropyran-2-ylisoxazol-5-yl]-3-buten-2-one 47 g of 1-triphenylphosphoranylidene-2-propanone were dissolved in 50 ml of dichloromethane, and 27 g of 5-formyl-3-tetrahydropyran-2-ylisoxazole were added. The reaction mixture was stirred for 1 day at room temperature and then evaporated down, the residue being stirred in methyl tert-butyl ether. After the triphenylphosphine oxide has been separated off, 43 g of a yellow oil remained.

c)
4-[3-Tert-butyl-5-methylisoxazolin-5-yl]-3-buten-2-one 35.0 g (0.21 mole) of 3-tert-butyl-5-formyl-5-methylisoxazoline were added dropwise to a solution of 79 g (0.25 mole) of 1-triphenylphosphoranylidene-2-propanone in 200 ml of dichloromethane. The reaction mixture was kept at 40° C. for 8 hours and then stirred with tert-butyl methyl ether. The residue was filtered off under suction and the filtrate was evaporated down to give 43 g of a yellow oil which slowly crystallized.

3. Preparation of the 3-hydroxy-2-cyclohexen-1-ones VIII.

a)
3-Hydroxy-5-[3-tetrahydrofur-3-ylisoxazol-5-yl]-2-cyclohexen-1-one 10.6 g of dimethyl malonate in 300 ml of methanol were initially taken, and 14.4 g of a 30% strength sodium ethylate solution in methanol were added at room temperature. Thereafter, 16.0 g of 4-[tetrahydrofur-3-ylisoxazol-5-yl]-3-buten-2-one were added and the mixture was stirred for 1 day at 25° C. The residue which remained after the solvent had been removed was taken up in 10% strength sodium hydroxide solution and stirred for 24 hours at 25° C. The sodium hydroxide phase was washed with methyl tert-butyl ether, acidified to pH 2 with concentrated hydrochloric acid and then heated at 85° C. for 2 hours. The solid formed was filtered off, washed with water and dried 12.3 g of a beige solid of melting point 142°-144° C. were obtained b)
5-[3-sec-Butyl-5-methylisoxazolin-5-yl]-3-hydroxy-2-cyclohexen-1-one 31.7 g (0.24 mole) of dimethyl malonate were dissolved in 300 ml of methanol, and 43.2 g (0.24 mole) of 30% strength sodium methylate solution in methanol rx were added at ≦30° C. Thereafter, a solution of 50.2 g (0.24 mole) of 4-[3-sec-butyl-5-methylisoxazolin-5-yl]-3-buten-2-one in 50 ml of methanol was added. After 24 hours at 25° C., the solvent was removed under reduced pressure.

The residue was taken up in 400 ml of 10% strength sodium hydroxide solution and the solution was stirred for 1 day at 25° C. The sodium hydroxide phase was extracted twice with tert-butyl methyl ether and acidified to pH 5 at 50° C. with concentrated hydrochloric acid. Stirring was then continued for 2 hours at 85° C. and the pH was brought to 3. The aqueous phase was extracted with dichloromethane, and the extract was washed with water, dried over sodium sulfate and evaporated down 56 g of a red oil were obtained.

4. Preparation of the 2-acyl-3-hydroxy-2-cyclohexen-1-ones II a)
2-Butyryl-3-hydroxy-5-[3-(tetrahydrofuryl)isoxazol-5-yl]-2-cyclohexen-1-one 12.0 g of the diketone from 3a) were dissolved in 300 ml of tetrahydrofuran, and 5.4 g of triethylamine and then 5.6 g of butyryl chloride were added. The reaction mixture was stirred for 24 hours at 25° C., after which water was added and the mixture was extracted with dichloromethane. The organic phase was washed once with water, dried and evaporated down 15.2 g of an orange oil remained; this oil was taken up in 150 ml of dichloromethane, and 3.0 g of 4-N,N-dimethylaminopyridine were added. After 3 days, the mixture was stirred into 10% strength hydrochloric acid. The organic phase was separated off, washed once with water, dried and evaporated down. 14.1 g of a yellow solid of melting point 102°-104° C. were obtained.

b)
5-(sec-Butyl-5-methylisoxazolin-5-yl)-2-butyryl-3-hydroxy-2-cyclohexen-1-one 28.0 g (0.11 mole) of the diketone according to 3b) were dissolved in 300 ml of tetrahydrofuran, and 13.1 g (0.13 mole) of triethylamine and 13.8 g (0.13 mole) of butyryl chloride were added. 10.2 g of a yellow solid of melting point 53°-55° C. were obtained by a procedure similar to the working-up steps described under 4a).

5. Preparation of the cyclohexenone oxime ether derivatives of the formula I a)
2-(1-Ethoxyiminobutyl)-3-hydroxy-5-[3-tetrahydrofur-3-ylisoxazol-5-yl]-2-cyclohexen-1-one A mixture of 3.0 g of the acyl compound according to 4a), 0.9 g of sodium bicarbonate, 1.1 g of ethoxyamine hydrochloride and 100 ml of methanol was stirred for 24 hours at 25° C., and then evaporated down, the residue was taken up in ethyl acetate and the solution was purified by chromatography.

2.5 g of a yellow solid of melting point 58°-60° C. were obtained (compound 3.9).

b)
2-(1-Ethoxyimino-n-butyl)-3-hydroxy-5-(3-isopropyl-5-methylisoxazolin-5-yl)-2-cyclohexen-1-one A mixture of 3.5 g (11 millimoles) of the acyl compound according to 4b), 1.0 g (12 millimoles) of sodium bicarbonate, 1.2 g (12 millimoles) of ethoxyamine hydrochloride and 100 ml of methanol was stirred for 24 hours at room temperature. The reaction mixture was evaporated down, the residue was taken up in 50 ml of 10% strength sodium hydroxide solution and the solution was washed with dichloromethane. The aqueous phase was acidified with concentrated hydrochloric acid, the precipitated solid was separated off and the filtrate was extracted twice with dichloromethane. The organic phase was dried over sodium sulfate and evaporated down. 3.3 g of a yellow solid of melting point 85° C. were obtained (compound 8.17).

The compounds of the formula I which are listed in the Table and characterized by their melting point (mp.) can be prepared in a similar manner. Tables 7 and 12 list the compounds which could not be isolated as a solid. Compounds for which no physical data are given can be obtained in a similar manner.

TABLE 1

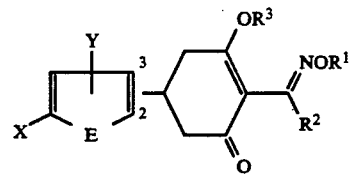

| Comp. No. | E | Bond in position | X | Y | R³ | R² | R¹ | m.p./°C. |
|---|---|---|---|---|---|---|---|---|
| 1.1 | S | 2 | 2-thienyl | H | H | n-propyl | ethyl | 51–52 |
| 1.2 | S | 2 | 2-thienyl | H | H | n-propyl | allyl | 53–55 |
| 1.3 | S | 2 | 2-thienyl | H | H | n-propyl | (E)-2-butenyl | 56–57 |
| 1.4 | S | 2 | 2-thienyl | H | H | n-propyl | (E)-3-chloro-2-propenyl | 65–67 |
| 1.5 | S | 2 | 2-thienyl | H | H | ethyl | ethyl | |
| 1.6 | S | 2 | 2-thienyl | H | H | ethyl | allyl | 47–48 |
| 1.7 | S | 2 | 2-thienyl | H | H | ethyl | (E)-2-butenyl | 75–77 |
| 1.8 | S | 2 | 2-thienyl | H | H | ethyl | (E)-3-chloro-2-propenyl | 58–61 |
| 1.9 | S | 2 | 5-chloro-2-thienyl | H | H | n-propyl | ethyl | |
| 1.10 | S | 2 | 5-chloro-2-thienyl | H | H | n-propyl | (E)-2-butenyl | |
| 1.11 | S | 2 | 5-chloro-2-thienyl | H | H | n-propyl | 2-butynyl | |

TABLE 2

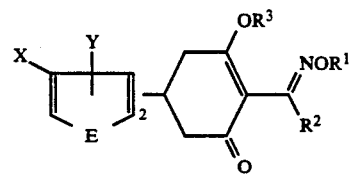

| Comp. No. | E | Bond in position | X | Y | R³ | R² | R¹ | m.p./°C. |
|---|---|---|---|---|---|---|---|---|
| 2.1 | S | 2 | 1-imidazolyl | H | H | ethyl | ethyl | |
| 2.2 | S | 2 | 1-imidazolyl | H | H | ethyl | allyl | |
| 2.3 | S | 2 | 1,3-thiazol-2-yl | 5-methyl | H | n-propyl | 2-fluoroethyl | |
| 2.4 | S | 2 | 1,3-thiazol-2-yl | 5-methyl | H | n-propyl | 2-propynyl | |
| 2.5 | S | 2 | 1,3-thiazol-2-yl | 5-methyl | H | n-propyl | (E)-2-butenyl | |
| 2.6 | O | 2 | cyclohexyl | H | H | ethyl | ethyl | |
| 2.7 | O | 2 | cyclohexyl | H | H | ethyl | (E)-3-chloro-2-propenyl | |
| 2.8 | O | 2 | cyclohexyl | H | H | n-propyl | allyl | |
| 2.9 | O | 2 | cyclohexyl | H | H | n-propyl | 5-chloro-2-thenyl | |
| 2.10 | O | 2 | 3-tetrahydrothiopyranyl | H | H | ethyl | (E)-2-butenyl | |
| 2.11 | O | 2 | 3-tetrahydrothiopyranyl | H | H | ethyl | (E)-3-chloro-2-propenyl | |
| 2.12 | O | 2 | 3-tetrahydrothiopyranyl | H | H | n-propyl | ethyl | |
| 2.13 | O | 2 | 3-tetrahydrothiopyranyl | H | H | n-propyl | 5-chloro-2-thenyl | |

TABLE 3

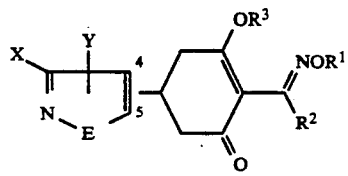

| Comp. No. | E | Bond in position | X | Y | R³ | R² | R¹ | m.p. °C. |
|---|---|---|---|---|---|---|---|---|
| 3.1 | O | 5 | 2-tetrahydrofuranyl | H | H | ethyl | ethyl | 83 |
| 3.2 | O | 5 | 2-tetrahydrofuranyl | H | H | ethyl | allyl | |
| 3.3 | O | 5 | 2-tetrahydrofuranyl | H | H | ethyl | (E)-2-butenyl | 86–87 |
| 3.4 | O | 5 | 2-tetrahydrofuranyl | H | H | ethyl | (E)-3-chloro-2-propenyl | 84 |
| 3.5 | O | 5 | 2-tetrahydrofuranyl | H | H | n-propyl | ethyl | |
| 3.6 | O | 5 | 2-tetrahydrofuranyl | H | H | n-propyl | allyl | |
| 3.7 | O | 5 | 2-tetrahydrofuranyl | H | H | n-propyl | (E)-2-butenyl | 56–57 |
| 3.8 | O | 5 | 2-tetrahydrofuranyl | H | H | n-propyl | (E)-3-chloro-2-propenyl | 67–68 |
| 3.9 | O | 5 | 3-tetrahydrofuranyl | H | H | n-propyl | ethyl | 58–60 |
| 3.10 | O | 5 | 3-tetrahydrofuranyl | H | H | n-propyl | allyl | 45–49 |

TABLE 3-continued

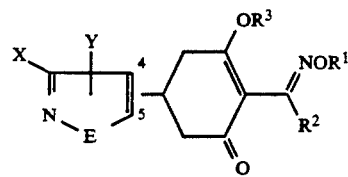

| Comp. No. | E | Bond in position | X | Y | R³ | R² | R¹ | m.p. °C. |
|---|---|---|---|---|---|---|---|---|
| 3.11 | O | 5 | 3-tetrahydrofuranyl | H | H | n-propyl | (E)-2-butenyl | |
| 3.12 | O | 5 | 3-tetrahydrofuranyl | H | H | n-propyl | (E)-3-chloro-2-propenyl | |
| 3.13 | O | 5 | 2-tetrahydropyranyl | H | H | ethyl | ethyl | 56–58 |
| 3.14 | O | 5 | 2-tetrahydropyranyl | H | H | ethyl | allyl | 47–48 |
| 3.15 | O | 5 | 2-tetrahydropyranyl | H | H | ethyl | (E)-2-butenyl | 93–94 |
| 3.16 | O | 5 | 2-tetrahydropyranyl | H | H | ethyl | (E)-3-chloro-2-propenyl | 101–102 |
| 3.17 | O | 5 | 2-tetrahydropyranyl | H | H | n-propyl | ethyl | |
| 3.18 | O | 5 | 2-tetrahydropyranyl | H | H | n-propyl | allyl | |
| 3.19 | O | 5 | 2-tetrahydropyranyl | H | H | n-propyl | (E)-2-butenyl | |
| 3.20 | O | 5 | 2-tetrahydropyranyl | H | H | n-propyl | (E)-3-chloro-2-propenyl | 74 |
| 3.21 | O | 5 | 3-tetrahydropyranyl | H | H | n-propyl | ethyl | 52–54 |
| 3.22 | O | 5 | 3-tetrahydropyranyl | H | H | n-propyl | (E)-2-butenyl | 53–55 |
| 3.23 | O | 5 | 4-tetrahydropyranyl | H | H | ethyl | ethyl | 131–133 |
| 3.24 | O | 5 | 4-tetrahydropyranyl | H | H | ethyl | allyl | 106–109 |
| 3.25 | O | 5 | 4-tetrahydropyranyl | H | H | ethyl | (E)-2-butenyl | 94–97 |
| 3.26 | O | 5 | 4-tetrahydropyranyl | H | H | ethyl | (E)-3-chloro-2-propenyl | 100–102 |
| 3.27 | O | 5 | 4-tetrahydropyranyl | H | H | n-propyl | ethyl | 108–109 |
| 3.28 | O | 5 | 4-tetrahydropyranyl | H | H | n-propyl | allyl | |
| 3.29 | O | 5 | 4-tetrahydropyranyl | H | H | n-propyl | (E)-2-butenyl | |
| 3.30 | O | 5 | 4-tetrahydropyranyl | H | H | n-propyl | (E)-3-chloro-2-propenyl | 75–77 |
| 3.31 | O | 5 | 3-tetrahydropyranyl | H | H | ethyl | ethyl | |
| 3.32 | O | 5 | 3-tetrahydropyranyl | H | H | ethyl | (E)-4-phenyl-2-butenyl | |
| 3.33 | O | 5 | 3-tetrahydropyranyl | ethyl | Na | n-propyl | ethyl | |
| 3.34 | O | 5 | 3-tetrahydropyranyl | ethyl | CO(CH₂)₃CH₃ | n-propyl | allyl | |
| 3.35 | O | 5 | 3-tetrahydropyranyl | H | Li | n-propyl | (E)-2-butenyl | |
| 3.36 | O | 5 | 1,3-dioxan-2-yl | H | H | n-propyl | allyl | |
| 3.37 | O | 5 | 1,3-dioxan-2-yl | H | H | n-propyl | (E)-3-chloro-2-propenyl | |
| 3.38 | O | 5 | 1,3-dioxan-2-yl | H | H | ethyl | ethyl | |
| 3.39 | O | 5 | 1,3-dioxan-2-yl | H | H | ethyl | 5-chloro-2-thenyl | |
| 3.40 | O | 5 | 5,5-dimethyl-1,3-dioxan-2-yl | H | H | ethyl | ethyl | |
| 3.41 | O | 5 | 5,5-dimethyl-1,3-dioxan-2-yl | H | H | ethyl | allyl | |
| 3.42 | O | 5 | 1,3-dioxolan-2-yl | H | H | n-propyl | ethyl | |
| 3.43 | O | 5 | 1,3-dioxolan-2-yl | H | H | n-propyl | (E)-2-butenyl | |
| 3.44 | O | 5 | 1,3-dioxolan-2-yl | H | H | ethyl | allyl | |
| 3.45 | O | 5 | 1,3-dithiolan-2-yl | H | H | ethyl | (E)-3-chloro-2-propenyl | |
| 3.46 | O | 5 | 1,3-dithiolan-2-yl | H | H | ethyl | 4-phenyl-2-butenyl | |
| 3.47 | O | 5 | 1,3-dithiolan-2-yl | H | H | n-propyl | ethyl | |
| 3.48 | O | 5 | 1,3-dithiolan-2-yl | H | K | n-propyl | allyl | |
| 3.49 | O | 5 | 1,3-dithiolan-2-yl | H | H | n-propyl | (E)-2-butenyl | |
| 3.50 | O | 5 | 2-furyl | H | H | ethyl | ethyl | 120–121 |
| 3.51 | O | 5 | 2-furyl | H | H | ethyl | allyl | 83 |
| 3.52 | O | 5 | 2-furyl | H | H | ethyl | (E)-2-butenyl | 109–110 |
| 3.53 | O | 5 | 2-furyl | H | H | ethyl | (E)-3-chloro-2-propenyl | 108–109 |
| 3.54 | O | 5 | 2-furyl | H | H | n-propyl | ethyl | oil |
| 3.55 | O | 5 | 2-furyl | H | H | n-propyl | allyl | 56–57 |
| 3.56 | O | 5 | 2-furyl | H | H | n-propyl | (E)-2-butenyl | 73–74 |
| 3.57 | O | 5 | 2-furyl | H | H | n-propyl | (E)-3-chloro-2-propenyl | 100–101 |
| 3.58 | O | 5 | 3-pyridyl | H | H | n-propyl | ethyl | 117–119 |
| 3.59 | O | 5 | 3-pyridyl | H | H | n-propyl | (E)-3-chloro-2-propenyl | |
| 3.60 | O | 5 | 3-pyridyl | H | H | n-propyl | (E)-4-(3-trifluoromethyl-phenyl)-2-butenyl | |
| 3.61 | O | 5 | 3-pyridyl | H | H | n-propyl | (E)-2-butenyl | 108–110 |
| 3.62 | O | 5 | 2-pyridyl | H | H | ethyl | ethyl | 73 |
| 3.63 | O | 5 | 2-pyridyl | H | H | ethyl | (E)-2-butenyl | 93 |
| 3.64 | O | 5 | 2-pyridyl | H | H | ethyl | (E)-4-(4-chlorophenyl)-2-butenyl | |
| 3.65 | O | 5 | 2-pyridyl | H | H | n-propyl | ethyl | 75 |
| 3.66 | O | 5 | 2-pyridyl | H | H | n-propyl | (E)-3-chloro-2-propenyl | 84 |
| 3.67 | O | 5 | 2-pyridyl | H | H | n-propyl | (E)-2-butenyl | 63–64 |
| 3.68 | O | 5 | 2-pyridyl | H | H | n-propyl | allyl | oil |
| 3.69 | O | 5 | 2-pyridyl | H | H | ethyl | allyl | 75–76 |
| 3.70 | O | 5 | 2-pyridyl | H | H | ethyl | (E)-3-chloro-2-propenyl | 112 |

TABLE 4

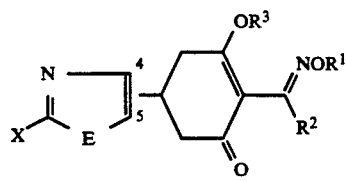

| Comp. No. | E | X | Bond position | $R^3$ | $R^2$ | $R^1$ | m.p./°C. |
|---|---|---|---|---|---|---|---|
| 4.1 | S | 4-pyridyl | 4 | H | ethyl | 2-chloroethyl | |
| 4.2 | S | 4-pyridyl | 4 | H | ethyl | (E)-3-chloro-2-propenyl | |
| 4.3 | S | 4-pyridyl | 4 | H | ethyl | 5-chloro-2-thenyl | |
| 4.4 | S | 4-pyridyl | 4 | H | n-propyl | ethyl | |
| 4.5 | O | cyclopropyl | 5 | Methyl | n-propyl | ethyl | |
| 4.6 | O | cyclopropyl | 5 | Methyl | n-propyl | (E)-2-butenyl | |
| 4.7 | O | cyclopropyl | 5 | Methyl | ethyl | ethyl | |
| 4.8 | S | 3-tetrahydrothiopyranyl | 5 | H | n-propyl | ethyl | |
| 4.9 | S | 3-tetrahydrothiopyranyl | 5 | H | n-propyl | 2-fluoroethyl | |
| 4.10 | S | 3-tetrahydrothiopyranyl | 5 | H | n-propyl | (E)-2-butenyl | |
| 4.11 | S | 3-tetrahydrothiopyranyl | 4 | H | ethyl | ethyl | |
| 4.12 | S | 3-tetrahydrothiopyranyl | 4 | H | ethyl | 2-butynyl | |
| 4.13 | S | 3-tetrahydrothiopyranyl | 4 | H | ethyl | (E)-4-(4-methylphenyl-2-butenyl | |
| 4.14 | S | 3-tetrahydrothiopyranyl | 4 | H | ethyl | (E)-4-(2-fluorophenyl)-2-butenyl | |

TABLE 5

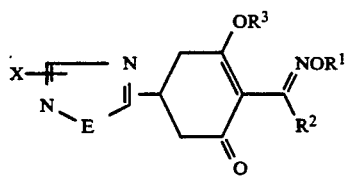

| Comp. No. | E | Bond in position | X | $R^3$ | $R^2$ | $R^1$ | m.p./°C. |
|---|---|---|---|---|---|---|---|
| 5.1 | O | 5 | cyclopropyl | H | n-propyl | ethyl | oil |
| 5.2 | O | 5 | cyclopropyl | H | n-propyl | allyl | oil |
| 5.3 | O | 5 | cyclopropyl | H | n-propyl | (E)-2-butenyl | oil |
| 5.4 | O | 5 | cyclopropyl | H | ethyl | ethyl | oil |
| 5.5 | O | 5 | cyclopropyl | H | ethyl | (E)-2-butenyl | oil |
| 5.6 | O | 5 | cyclopentyl | H | n-propyl | ethyl | |
| 5.7 | O | 5 | cyclopentyl | H | n-propyl | (E)-3-chloro-2-propenyl | |
| 5.8 | O | 5 | cyclopentyl | H | ethyl | ethyl | |
| 5.9 | O | 5 | cyclohexyl | H | ethyl | 2-butynyl | |
| 5.10 | O | 5 | cyclohexyl | H | ethyl | allyl | |
| 5.11 | O | 5 | cyclohexyl | H | n-propyl | (E)-3-chloro-2-propenyl | |
| 5.12 | O | 5 | 3-tetrahydrothiopyranyl | H | n-propyl | ethyl | |
| 5.13 | O | 5 | 3-tetrahydrothiopyranyl | H | n-propyl | allyl | |
| 5.14 | O | 5 | 3-tetrahydrothiopyranyl | H | n-propyl | 2-propynyl | |
| 5.15 | O | 5 | 2-furyl | H | ethyl | 5-chloro-2-thenyl | |
| 5.16 | O | 5 | 2-furyl | H | ethyl | (E)-4-phenyl-2-butenyl | |
| 5.17 | O | 5 | 2-pyridyl | H | n-propyl | 2-fluoroethyl | |
| 5.18 | O | 5 | 2-pyridyl | H | n-propyl | ethyl | |
| 5.19 | S | 5 | cyclopropyl | H | n-propyl | ethyl | |
| 5.20 | S | 5 | cyclopropyl | H | ethyl | allyl | |
| 5.21 | S | 5 | cyclopropyl | H | ethyl | (E)-2-butenyl | |
| 5.22 | O | 5 | cyclopropyl | H | ethyl | allyl | |
| 5.23 | O | 5 | cyclohexyl | H | n-propyl | ethyl | oil |
| 5.24 | O | 5 | cyclohexyl | H | n-propyl | allyl | oil |
| 5.25 | O | 5 | cyclohexyl | H | n-propyl | (E)-2-butenyl | oil |
| 5.26 | O | 5 | cyclopentyl | H | n-propyl | (E)-2-butenyl | oil |

TABLE 6

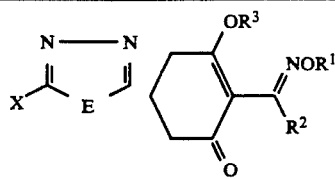

| Comp. No. | E | X | R³ | R² | R¹ | m.p./°C |
|---|---|---|---|---|---|---|
| 6.1 | O | cyclopentyl | H | ethyl | ethyl | |
| 6.2 | O | cyclopentyl | H | ethyl | allyl | |
| 6.3 | O | cyclopentyl | H | ethyl | (E)-4-(3-methylphenyl)-2-butenyl | |
| 6.4 | O | 3-tetrahydrothiopyranyl | H | ethyl | ethyl | |
| 6.5 | O | 3-tetrahydrothiopyranyl | H | n-propyl | ethyl | |
| 6.6 | O | 3-tetrahydrothiopyranyl | H | n-propyl | (E)-3-chloro-2-propenyl | |
| 6.7 | S | cyclopropyl | H | ethyl | allyl | |
| 6.8 | S | cyclopropyl | H | n-propyl | 2-propynyl | |
| 6.9 | S | cyclopropyl | H | n-propyl | (E)-4-(3-nitrophenyl)-2-butenyl | |
| 6.10 | S | 2-furyl | H | ethyl | ethyl | |
| 6.11 | S | 2-furyl | H | ethyl | (E)-2-butenyl | |
| 6.12 | S | 2-furyl | Li | ethyl | 5-chloro-2-thenyl | |

TABLE 7

The $^1$H-NMR spectra were taken up in deuteriochloroform or hexadeuteriodimethyl sulfoxide as solvent with tetramethylsilane as internal sandard. The chemical shifts were registered in ppm. The multiplicities are given as follows:
s = singlet, d = doublet, t = triplet,
q = quartet, m = multiplet.

$^1$H-NMR data

| Comp. | Chem. shift |
|---|---|
| 1.5 | 1.16(t, 3H), 1,34(t, 3H), 3.59(m, 1H), 4.12(q, 2H) |
| 3.2 | 1.14(t, 3H), 2.93(t, 2H), 4.56(d, 2H), 6.08(s, 1H) |
| 3.5 | 1.03(t, 3H), 1.39(t, 3H), 4.17(q, 2H), 6.13(s, 1H) |
| 3.6 | 1.02(t, 3H), 1.61("6", 2H), 4.46(d, 2H), 6.13(s, 1H) |
| 3.11 | 0.97(t, 3H), 1.77(d, 3H), 4.46(d, 2H), 5.97(s 1H) |
| 3.12 | 0.96(t, 3H), 1.53("6", 2H), 2.88(t 2H), 4.54(d, 2H), 5, 97(s, 1H) |
| 3.17 | 0.96(t, 3H), 1.30(t, 3H), 4.10(q, 2H), 6.11(s, 1H) |
| 3.18 | 0.97(t, 3H), 4.56(d, 2H), 6.12(s, 1H) |
| 3.19 | 0.92(t, 3H), 1.76(d, 3H), 4.44(d, 2H), 6.10(s, 1H) |
| 3.28 | 0.96(t, 3H), 2.94(t, 2H), 4.55(d, 2H), 5.93(s, 1H) |
| 3.29 | 0.97(t, 3H), 1.76(d, 3H), 4.45(d, 2H), 5.93(s, 1H) |
| 3.54 | 1.0 (t, 3H), 1.35(t, 3H), 2.97(t, 2H), 4.14(q, 2H) 6, 35(2, 1H) |
| 5.1 | 0.97(t, 3H), 1.33(t, 3H), 2.94(t, 2H), 4.12(q, 2H) |
| 5.2 | 0.96(t, 3H), 2.92(t, 2H), 4.55(d, 2H) |
| 5.3 | 0.95(t, 3H), 4.47(d, 2H), |
| 5.4 | 1.14(t, 3H), 1.35(t, 3H), 4.13(q, 2H) |
| 5.5 | 1.13(t, 3H), 1.77(d, 3H), 4.45(d, 2H) |

TABLE 8

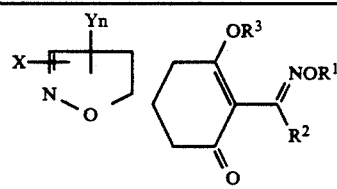

| Comp. No. | Yn | X | R³ | R² | R¹ | m.p. °C |
|---|---|---|---|---|---|---|
| 8.1 | 3-ethyl, 5-methyl | H | H | n-propyl | ethyl | 55–56 |
| 8.2 | 3-ethyl, 5-methyl | H | H | n-propyl | allyl | oil |
| 8.3 | 3-ethyl, 5-methyl | H | H | n-propyl | (E)-2-butenyl | oil |
| 8.4 | 3-ethyl, 5-methyl | H | H | n-propyl | (E)-3-chloro-2-propenyl | oil |
| 8.5 | 3-i-propyl | H | H | ethyl | ethyl | oil |
| 8.6 | 3-i-propyl | H | H | ethyl | allyl | oil |
| 8.7 | 3-i-propyl | H | H | ethyl | (E)-2-butenyl | oil |
| 8.8 | 3-i-propyl | H | H | ethyl | (E)-3-chloro-2-propenyl | oil |
| 8.9 | 3-i-propyl | H | H | n-propyl | ethyl | oil |
| 8.10 | 3-i-propyl | H | H | n-propyl | allyl | oil |
| 8.11 | 3-i-propyl | H | H | n-propyl | (E)-2-butenyl | oil |
| 8.12 | 3-i-propyl | H | H | n-propyl | (E)-3-chloro-2-propenyl | oil |
| 8.13 | 3-i-propyl, 5-methyl | H | H | ethyl | ethyl | 65 |
| 8.14 | 3-i-propyl, 5-methyl | H | H | ethyl | allyl | 58 |
| 8.15 | 3-i-propyl, 5-methyl | H | H | ethyl | (E)-2-butenyl | 67–68 |
| 8.16 | 3-i-propyl, 5-methyl | H | H | ethyl | (E)-3-chloro-2-propenyl | oil |
| 8.17 | 3-i-propyl, 5-methyl | H | H | n-propyl | ethyl | 85 |
| 8.18 | 3-i-propyl, 5-methyl | H | H | n-propyl | allyl | 65–66 |
| 8.19 | 3-i-propyl, 5-methyl | H | H | n-propyl | (E)-2-butenyl | 77–78 |
| 8.20 | 3-i-propyl, 5-methyl | H | H | n-propyl | (E)-3-chloro-2-propenyl | 80–81 |
| 8.21 | 3,5-di-iso-propyl | H | H | ethyl | ethyl | |

TABLE 8-continued

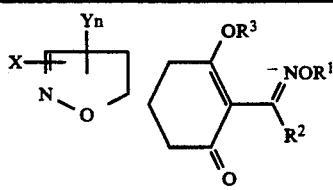

| Comp. No. | Yn | X | R³ | R² | R¹ | m.p. °C. |
|---|---|---|---|---|---|---|
| 8.22 | 3,5-di-iso-propyl | H | H | ethyl | allyl | |
| 8.23 | 3,5-di-iso-propyl | H | H | ethyl | (E)-2-butenyl | |
| 8.24 | 3,5-di-iso-propyl | H | H | ethyl | (E)-3-chloro-2-propenyl | |
| 8.25 | 3,5-di-iso-propyl | H | H | n-propyl | ethyl | |
| 8.26 | 3,5-di-iso-propyl | H | H | n-propyl | allyl | |
| 8.27 | 3,5-di-iso-propyl | H | H | n-propyl | (E)-2-butenyl | |
| 8.28 | 3,5-di-iso-propyl | H | H | n-propyl | (E)-3-chloro-2-propenyl | |
| 8.29 | 3-i-propyl, 5-benzyl | H | H | ethyl | ethyl | 65–68 |
| 8.30 | 3-i-propyl, 5-benzyl | H | H | ethyl | allyl | oil |
| 8.31 | 3-i-propyl, 5-benzyl | H | H | ethyl | (E)-2-butenyl | oil |
| 8.32 | 3-i-propyl, 5-benzyl | H | H | ethyl | (E)-3-chloro-2-propenyl | oil |
| 8.33 | 3-i-propyl, 5-benzyl | H | H | n-propyl | ethyl | 89–92 |
| 8.34 | 3-i-propyl, 5-benzyl | H | Li | n-propyl | ethyl | |
| 8.35 | 3-i-propyl, 5-benzyl | H | H | n-propyl | allyl | 83–85 |
| 8.36 | 3-i-propyl, 5-benzyl | H | H | n-propyl | (E)-2-butenyl | oil |
| 8.37 | 3-i-propyl, 5-benzyl | H | H | n-propyl | (E)-3-chloro-2-propenyl | oil |
| 8.38 | 3-i-propyl, 5-benzyl | H | H | n-propyl | 5-chloro-2-thenyl | |
| 8.39 | 3-i-butyl, 5-methyl | H | H | ethyl | ethyl | 61–63 |
| 8.40 | 3-i-butyl, 5-methyl | H | H | ethyl | allyl | oil |
| 8.41 | 3-i-butyl, 5-methyl | H | H | ethyl | (E)-2-butenyl | 48–50 |
| 8.42 | 3-i-butyl, 5-methyl | H | H | ethyl | (E)-3-chloro-2-propenyl | oil |
| 8.43 | 3-i-butyl, 5-methyl | H | H | n-propyl | ethyl | 66–68 |
| 8.44 | 3-i-butyl, 5-methyl | H | H | n-propyl | allyl | 63–65 |
| 8.45 | 3-i-butyl, 5-methyl | H | H | n-propyl | (E)-2-butenyl | 57–59 |
| 8.46 | 3-i-butyl, 5-methyl | H | H | n-propyl | (E)-3-chloro-2-propenyl | oil |
| 8.47 | 3-s-butyl, 5-methyl | H | Li | ethyl | ethyl | |
| 8.48 | 3-s-butyl, 5-methyl | H | H | ethyl | ethyl | oil |
| 8.49 | 3-s-butyl, 5-methyl | H | H | ethyl | allyl | oil |
| 8.50 | 3-s-butyl, 5-methyl | H | H | ethyl | (E)-2-butenyl | oil |
| 8.51 | 3-s-butyl, 5-methyl | H | H | ethyl | (E)-3-chloro-2-propenyl | oil |
| 8.52 | 3-s-butyl, 5-methyl | H | H | ethyl | (E)-4-phenyl-2-butenyl | |
| 8.53 | 3-s-butyl, 5-methyl | H | H | n-propyl | ethyl | 56–59 |
| 8.54 | 3-s-butyl, 5-methyl | H | H | n-propyl | allyl | |
| 8.55 | 3-s-butyl, 5-methyl | H | H | n-propyl | (E)-2-butenyl | oil |
| 8.56 | 3-s-butyl, 5-methyl | H | H | n-propyl | (E)-3-chloro-2-propenyl | oil |
| 8.57 | 3-s-butyl, 5-methyl | H | H | n-propyl | (E)-4-(4-methylphenyl)-2-butenyl | |
| 8.58 | 3-t-butyl, 5-methyl | H | H | ethyl | ethyl | |
| 8.59 | 3-t-butyl, 5-methyl | H | H | ethyl | allyl | |
| 8.60 | 3-t-butyl, 5-methyl | H | H | ethyl | (E)-2-butenyl | |
| 8.61 | 3-t-butyl, 5-methyl | H | H | ethyl | (E)-3-chloro-2-propenyl | |
| 8.62 | 3-t-butyl, 5-methyl | H | Na | ethyl | (E)-3-chloro-2-propenyl | |
| 8.63 | 3-t-butyl, 5-methyl | H | H | ethyl | 3-chlorobenzyl | |
| 8.64 | 3-t-butyl, 5-methyl | H | H | n-propyl | ethyl | |
| 8.65 | 3-t-butyl, 5-methyl | H | H | n-propyl | allyl | |
| 8.66 | 3-t-butyl, 5-methyl | H | H | n-propyl | (E)-2 butenyl | |
| 8.67 | 3-t-butyl, 5-methyl | H | H | n-propyl | (E)-3-chloro-2-propenyl | |
| 8.68 | 3-t-butyl, 5-methyl | H | H | n-propyl | methoxymethyl | |
| 8.69 | 3-t-butyl, 5-methyl | H | H | n-propyl | (E)-4-(3-trifluoromethylphenyl)-2-butenyl | |
| 8.70 | 3-(1-methoxyethyl), 5-methyl | H | H | ethyl | ethyl | |
| 8.71 | 3-(1-methoxyethyl), 5-methyl | H | H | ethyl | allyl | |
| 8,72 | 3-(1-methoxyethyl), 5-methyl | H | H | ethyl | (E)-2-butenyl | |
| 8.73 | 3-(1-methoxyethyl), 5-methyl | H | H | ethyl | (E)-3-chloro-2-propenyl | |
| 8.74 | 3-(1-methoxyethyl), 5-methyl | H | H | ethyl | 3-chloropropyl | |
| 8.75 | 3-(1-methoxyethyl), 5-methyl | H | H | n-propyl | ethyl | |
| 8.76 | 3-(1-methoxyethyl), 5-methyl | H | H | n-propyl | allyl | |
| 8.77 | 3-(1-methoxyethyl), 5-methyl | H | H | n-propyl | (E)-2-butenyl | |
| 8.78 | 3-(1-methoxyethyl), 5-methyl | H | H | n-propyl | (E)-3-chloro-2-propenyl | |
| 8.79 | 3-(1-methoxyethyl), 5-methyl | H | H | n-propyl | (E)-4-(4-fluorophenyl)-2-butenyl | |

TABLE 9

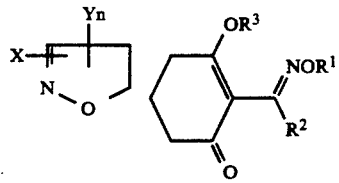

| Comp. No. | X | Yn | R³ | R² | R¹ | m.p. °C. |
|---|---|---|---|---|---|---|
| 9.1 | 3-cyclopropyl | 5-methyl | H | ethyl | ethyl | |
| 9.2 | 3-cyclopropyl | 5-methyl | H | ethyl | (E)-2-butenyl | |
| 9.3 | 3-cyclopropyl | 5-methyl | H | ethyl | (E)-3-chloro-2-propenyl | |
| 9.4 | 3-cyclopropyl | 5-methyl | H | ethyl | 5-chloro-2-thenyl | |
| 9.5 | 3-cyclopropyl | 5-methyl | H | ethyl | (E)-4-(4-chlorophenyl)-2-butenyl | |
| 9.6 | 3-cyclopentyl | 5-methyl | H | ethyl | ethyl | 75 |
| 9.7 | 3-cyclopentyl | 5-methyl | H | ethyl | allyl | 64 |
| 9.8 | 3-cyclopentyl | 5-methyl | H | ethyl | (E)-2-butenyl | 61 |
| 9.9 | 3-cyclopentyl | 5-methyl | H | ethyl | (E)-3-chloro-2-propenyl | oil |
| 9.10 | 3-cyclopentyl | 5-methyl | H | ethyl | 2-methoxyethyl | |
| 9.11 | 3-cyclopentyl | 5-methyl | H | n-propyl | ethyl | 72 |
| 9.12 | 3-cyclopentyl | 5-methyl | H | n-propyl | allyl | 52–53 |
| 9.13 | 3-cyclopentyl | 5-methyl | H | n-propyl | (E)-2-butenyl | 66 |
| 9.14 | 3-cyclopentyl | 5-methyl | H | n-propyl | (E)-3-chloro-2-propenyl | 67–68 |
| 9.15 | 3-cyclopentyl | 5-methyl | H | n-propyl | 4-fluorobenzyl | |
| 9.16 | 3-cyclohexyl | 5-methyl | H | ethyl | ethyl | |
| 9.17 | 3-cyclohexyl | 5-methyl | H | ethyl | (E)-2-butenyl | |
| 9.18 | 3-cyclohexyl | 5-methyl | H | n-propyl | ethyl | |
| 9.19 | 3-cyclohexyl | 5-methyl | H | n-propyl | 2-thenyl | |
| 9.20 | 3-cyclohexyl | 5-methyl | H | n-propyl | 3-chloropropyl | |
| 9.21 | 3-(3-tetrahydropyranyl) | 5-methyl | H | ethyl | ethyl | |
| 9.22 | 3-(3-tetrahydropyranyl) | 5-methyl | H | ethyl | allyl | |
| 9.23 | 3-(3-tetrahydropyranyl) | 5-methyl | H | ethyl | (E)-2-butenyl | |
| 9.24 | 3-(3-tetrahydropyranyl) | 5-methyl | H | ethyl | (E)-3-chloro-2-propenyl | |
| 9.25 | 3-(3-tetrahydropyranyl) | 5-methyl | H | ethyl | 4-methylbenzyl | |
| 9.26 | 3-(3-tetrahydropyranyl) | 5-methyl | H | n-propyl | ethyl | |
| 9.27 | 3-(3-tetrahydropyranyl) | 5-methyl | H | n-propyl | allyl | |
| 9.28 | 3-(3-tetrahydropyranyl) | 5-methyl | H | n-propyl | (E)-2-butenyl | |
| 9.29 | 3-(3-tetrahydropyranyl) | 5-methyl | H | n-propyl | (E)-3-chloropropenyl | |
| 9.30 | 3-(3-Tetrahydropyranyl) | 5-methyl | H | n-propyl | (E)-4-(4-trifluoromethylphenyl)-2-butenyl | |
| 9.31 | 3-(3-Tetrahydrothiopyranyl) | 4-methyl, 5-ethyl | H | ethyl | ethyl | |
| 9.32 | 3-(3-Tetrahydrothiopyranyl) | 4-methyl, 5-ethyl | H | ethyl | allyl | |
| 9.33 | 3-(3-Tetrahydrothiopyranyl) | 4-methyl, 5-ethyl | H | n-propyl | ethyl | |
| 9.34 | 3-(3-tetrahydrothiopyranyl) | 4-methyl, 5-ethyl | H | n-propyl | (E)-3-chloro-2-propenyl | |

TABLE 10

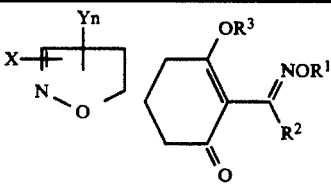

| Comp. No. | X | Yn | R³ | R² | R¹ | m.p. °C. |
|---|---|---|---|---|---|---|
| 10.1 | 3-phenyl | 5-ethyl | H | ethyl | ethyl | |
| 10.2 | 3-phenyl | 5-ethyl | Na | ethyl | allyl | |
| 10.3 | 3-phenyl | 5-ethyl | H | ethyl | (E)-2-butenyl | |
| 10.4 | 3-phenyl | 5-ethyl | H | n-propyl | 5-chloro-2-thenyl | |
| 10.5 | 3-(2-chlorophenyl) | 5-methyl | H | ethyl | ethyl | |
| 10.6 | 3-(2-chlorophenyl) | 5-methyl | H | ethyl | allyl | |
| 10.7 | 3-(2-chlorophenyl) | 5-methyl | H | ethyl | (E)-2-butenyl | |
| 10.8 | 3-(2-chlorophenyl) | 5-methyl | H | ethyl | (E)-3-chloro-2-propenyl | |
| 10.9 | 3-(2-chlorophenyl) | 5-methyl | H | n-propyl | ethyl | |
| 10.10 | 3-(2-chlorophenyl) | 5-methyl | H | n-propyl | allyl | |
| 10.11 | 3-(2-chlorophenyl) | 5-methyl | H | n-propyl | (E)-2-butenyl | |
| 10.12 | 3-(2-chlorophenyl) | 5-methyl | H | n-propyl | (E)-3-chloro-2-propenyl | |
| 10.13 | 3-(2-methoxyphenyl) | 5-methyl | H | ethyl | ethyl | |
| 10.14 | 3-(2-methoxyphenyl) | 5-methyl | H | ethyl | allyl | |
| 10.15 | 3-(2-methoxyphenyl) | 5-methyl | H | ethyl | (E)-2-butenyl | |
| 10.16 | 3-(2-methoxyphenyl) | 5-methyl | H | ethyl | (E)-3-chloro-2-propenyl | |
| 10.17 | 3-(2-methoxyphenyl) | 5-methyl | H | ethyl | 2-butynyl | |
| 10.18 | 3-(2-methoxyphenyl) | 5-methyl | H | n-propyl | ethyl | |
| 10.19 | 3-(2-methoxyphenyl) | 5-methyl | H | n-propyl | allyl | |
| 10.20 | 3-(2-methoxyphenyl) | 5-methyl | H | n-propyl | (E)-2-butenyl | |

TABLE 10-continued

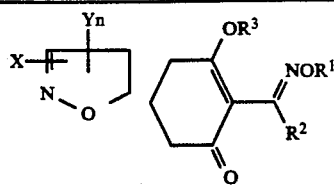

| Comp. No. | X | Yn | R³ | R² | R¹ | m.p. °C. |
|---|---|---|---|---|---|---|
| 10.21 | 3-(2-methoxyphenyl) | 5-methyl | H | n-propyl | (E)-3-chloro-2-propenyl | |
| 10.22 | 3-(2-methoxyphenyl) | 5-methyl | H | n-propyl | 2-fluoroethyl | |
| 10.23 | 3-(2-pyridyl) | 5-methyl | H | ethyl | ethyl | |
| 10.24 | 3-(2-pyridyl) | 5-methyl | H | ethyl | (E)-2-butenyl | |
| 10.25 | 3-(2-pyridyl) | 5-methyl | H | ethyl | (E)-3-chloro-2-propenyl | |
| 10.26 | 3-(2-pyridyl) | 5-methyl | H | n-propyl | ethyl | |
| 10.27 | 3-(2-pyridyl) | 5-methyl | H | n-propyl | allyl | |
| 10.28 | 3-(2-pyridyl) | 5-methyl | H | n-propyl | 2-propynyl | |
| 10.29 | 3-(2-furyl) | 5-i-propyl | H | n-propyl | ethyl | |
| 10.30 | 3-(2-furyl) | 5-i-propyl | H | n-propyl | 5-chloro-2-thenyl | |
| 10.31 | 3-(2-furyl) | 5-i-propyl | H | n-propyl | (E)-4-(4-chlorophenyl)-2-butenyl | |

TABLE 11

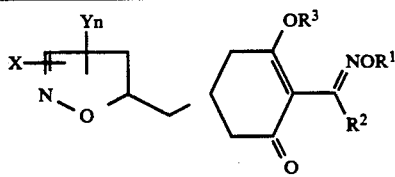

| Comp. No. | X | Yn | R³ | R² | R¹ | m.p. °C. |
|---|---|---|---|---|---|---|
| 11.1 | H | 5-methyl, 3-i-propyl | H | ethyl | ethyl | |
| 11.2 | H | 5-methyl, 3-i-propyl | H | ethyl | (E)-2-butenyl | |
| 11.3 | H | 5-methyl, 3-i-propyl | H | ethyl | (E)-3-chloro-2-propenyl | |
| 11.4 | H | 5-methyl, 3-i-propyl | H | n-propyl | ethyl | |
| 11.5 | H | 5-methyl, 3-i-propyl | H | n-propyl | allyl | |
| 11.6 | H | 5-methyl, 3-i-propyl | H | n-propyl | 5-chloro-2-thenyl | |

TABLE 12

The $^1$H-NMR spectra were taken up in deuteriochloroform or hexadeuteriodimethyl sulfoxide as solvent with tetramethylsilane as internal standard. The chemical shifts were registered in ppm. The multiplicities are given as follows:
s = singlet, d = doublet, t = triplet,
q = quartet, m = multiplet.

| Compound | Chemical shift [ppm] |
|---|---|
| 8.2 | 0.98(t, 3H), 1.18(t, 3H), 1.57("6", 2H), 2.37(q, 2H), 4.54(d, 2H) |
| 8.3 | 0.95(t, 3H), 1.17(t, 3H), 1.37("s", 3H), 1.76(d, 3H), 2.34(q, 2H), 4.45(d, 2H) |
| 8.4 | 0.95(t, 3H), 1.17(t, 3H), 1.39("s", 3H), 2.35(q, 2H), 4.52(d, 2H), 6.36(d, 1H) |
| 8.5 | 1.14(t, 3H), 1.19(d, 6H), 1.33(t, 3H), 2.92(q, 2H), 4.12(q, 2H) |
| 8.6 | 1.17(t, 3H), 1.21(d, 6H), 2.95(q, 2H), 4.57(d, 2H) |
| 8.7 | 1.17(t, 3H), 1.21(d, 6H), 1.81(d, 3H), 2.95(q, 2H), 4.48(d, 2H) |
| 8.8 | 1.14(t, 3H), 1.18(d, 6H), 2.88(q, 2H), 4.52(d, 2H), 6.35(d, 1H) |
| 8.9 | 0.97(t, 3H), 1.20(d, 6H), 1.56("6", 2H), 4.12(q, 2H) |
| 8.10 | 0.98(t, 3H), 1.19(d, 6H), 4.55(q, 2H) |
| 8.11 | 0.96(t, 3H), 1.18(d, 6H), 1.55("6", 2H), 1.78(d, 3H), 4.44(d, 2H) |
| 8.12 | 0.94(t, 3H), 1.18(d, 6H), 1.53("6", 2H), 4.49(d, 2H), 6.33(d, 1H) |
| 8.16 | 1.16(t, 3H), 1.20(d, 6H), 1.4("s", 3H), 4.53(d, 2H), 6.47(d, 1H) |

The herbicidal action of the cyclohexenone derivatives of the formula I is demonstrated by the following greenhouse experiments:

The vessels employed were plastic flowerpots having a volume of 300 cm³ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles. The application rate was 0.5 kg/ha.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 15 cm before being treated. In this treatment method, either plants which had been sown in the pots and grown there were selected, or they were cultivated separated as seedlings and transplanted to the pots a few days before being treated. The application rates for postemergence treatment were 0.125 and 0.25 kg/ha. No covers were placed on the vessels in this method.

The pots were set up in the greenhouse, species from warmer climates in warmer areas (20° to 35° C.) and species from moderate climates at 10° to 25° C. The experiments were run for from 2 to 4 weeks. During this time the plants were tended and their reactions to the various treatments assessed. The assessment scale was 0 to 100, 100 denoting nonemergence or complete destruction of at least the visible plant parts, and 0 denoting no damage or normal growth.

The plants employed for the experiments were Avena fatua, Digitaria sanguinalis, Echinochloa crus-galli, Lolium multiflorum, Medicago sativa, Setaria viridis, Sinapis alba, Triticum aestivum and Zea mays.

On preemergence application of 0.5 kg/ha, active ingredients 8.20 and 8.16 had a strong herbicidal action on grassy plants; mustard as an example of a broadleaved species remained undamaged.

For combating grassy vegetation, compounds 3.23 and 3.24 were suitable at a postemergence rate of 0.25 kg/ha, and compounds 8.75 and 8.77 at a postemergence rate of 0.125 kg/ha. Broadleaved crops—as illustrated by alfalfa—remained undamaged. The novel active ingredients have a selective herbicidal action.

Active ingredients 3.22 and 3.21 may be used postemergence at a rate of 0.125 kg/ha for combating unwanted grassy species in wheat. The cop plants suffer no damage.

We claim:
1. Cyclohexenone derivatives of the following formula:

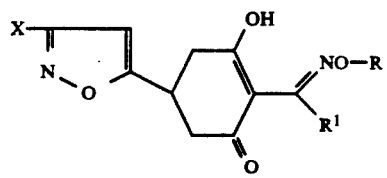

wherein:
X is 2-tetrahydrofuranyl, 3-tetrahydrofuranyl, 2-tetrahydropyranyl, 3-tetrahydropyranyl or 4-tetrahydropyranyl;
R is ethyl, allyl, 2-butenyl or 3-chlor-2-propenyl; and
$R^1$ is ethyl or n-propyl.

2. A compound of claim 1 wherein X is 2-tetrahydrofuranyl, R is (E)-2-butenyl, and $R^1$ is n-propyl.

3. A herbicidal composition containing a cyclohexenone derivative as set forth in claim 1.

4. A process for combating the growth of unwanted plants, wherein the unwanted plants and/or their habitat are treated with a herbicidally effective amount of a cyclohexenone derivative of the formula I as set forth in claim 1.

* * * * *

UNITED STATES PATENT AND TRADEMARK OFFICE
CERTIFICATE OF CORRECTION

PATENT NO. : 5,201,935
DATED : April 13, 1993
INVENTOR(S) : KOLASSA et al.

It is certified that error appears in the above-identified patent and that said Letters Patent is hereby corrected as shown below:

On the title page: Item [75] Inventors:

"Juergen Kasi" should read -- Juergen Kast --

Signed and Sealed this

Twenty-eighth Day of December, 1993

*Attest:*

BRUCE LEHMAN

*Attesting Officer*     *Commissioner of Patents and Trademarks*